US012605568B2

(12) United States Patent
Yoo et al.

(10) Patent No.: US 12,605,568 B2
(45) Date of Patent: Apr. 21, 2026

(54) HIGH-INTENSITY FOCUSED ULTRASOUND DEVICE AND METHOD FOR CONTROLLING TRANSDUCER MOVING PIEZOELECTRIC DEVICE USED IN THE SAME

(71) Applicant: CLASSYS INC., Seoul (KR)

(72) Inventors: Seon Uk Yoo, Osan-si (KR); Suk Ki Hong, Suwon-si (KR)

(73) Assignee: CLASSYS INC., Seoul (KR)

( * ) Notice: Subject to any disclaimer, the term of this patent is extended or adjusted under 35 U.S.C. 154(b) by 569 days.

(21) Appl. No.: 17/726,568

(22) Filed: Apr. 22, 2022

(65) Prior Publication Data

US 2022/0241618 A1 Aug. 4, 2022

Related U.S. Application Data

(63) Continuation of application No. 16/270,599, filed on Feb. 8, 2019, now abandoned.

(30) Foreign Application Priority Data

Sep. 13, 2018 (KR) ........................ 10-2018-0109583

(51) Int. Cl.
*A61N 7/00* (2006.01)

(52) U.S. Cl.
CPC ........ *A61N 7/00* (2013.01); *A61N 2007/0034* (2013.01); *A61N 2007/0073* (2013.01)

(58) Field of Classification Search
CPC ......................... A61N 7/00; A61N 2007/0034
See application file for complete search history.

(56) References Cited

U.S. PATENT DOCUMENTS

| | | | |
|---|---|---|---|
| 4,936,307 A | 6/1990 | Saito et al. | |
| 2015/0094595 A1 | 4/2015 | Havel et al. | |
| 2016/0243382 A1* | 8/2016 | Jo | A61B 5/065 |
| 2017/0303895 A1* | 10/2017 | Park | A61N 7/02 |
| 2018/0133470 A1* | 5/2018 | Park | A61N 5/0616 |

FOREIGN PATENT DOCUMENTS

| | | | |
|---|---|---|---|
| CN | 110191679 A | 8/2019 | |
| KR | 10-2016-0103760 A | 9/2016 | |
| KR | 10-1750444 B1 | 6/2017 | |
| KR | 10-1756618 B1 | 7/2017 | |
| KR | 10-2017-0095550 A | 8/2017 | |
| KR | 20170095550 A | * | 8/2017 |

OTHER PUBLICATIONS

KR 101673113 (Year: 2016).*

* cited by examiner

*Primary Examiner* — Keith M Raymond
*Assistant Examiner* — Adam D. Kolkin
(74) *Attorney, Agent, or Firm* — Bridgeway IP Law Group, PLLC; Jihun Kim

(57) ABSTRACT

A high-intensity focused ultrasound (HIFU) device and a method for controlling the transducer moving piezoelectric device achieve accurate and stable control as to movement of a transducer and a treatment position by use of a transducer moving piezoelectric device configured to have a compact size in accordance with a great reduction in the size of a handpiece.

4 Claims, 12 Drawing Sheets

- Conventional Art -

(a)

(b)

(a)

(b)

HIGH-INTENSITY FOCUSED ULTRASOUND DEVICE AND METHOD FOR CONTROLLING TRANSDUCER MOVING PIEZOELECTRIC DEVICE USED IN THE SAME

CROSS REFERENCE TO PRIOR APPLICATION

This application is a continuation application of U.S. patent application Ser. No. 16/270,599 filed on Feb. 8, 2019, which claims priority to Korean Patent Application No. 10-2018-0109583 filed on Sep. 13, 2018, which are all hereby incorporated by reference in their entirety.

ACKNOWLEDGEMENTS

[This work was supported by the National Innovation Project]
[Managing Department] Gyeonggi-do Provincial Government
[Research Management Agency] Gyeonggi Technopark
[Research Project Name] Export business IP convergence development support project, 2018
[Research Project Title] High Intensity Focused Ultrasound Stimulation System (Skin care medical device)
[Beneficiary] ILOODA Corporation
[Subject Performing agency] LEMONYELLOW Corporation
[Participation agency] CDR ASSOCIATES Corporation
[Participation agency] JOOWON Patent law Corporation
[Participation agency] H&H INTERNATIONAL patent law Corporation
[Research Period] Oct. 19, 2018~Feb. 15, 2019

BACKGROUND OF THE INVENTION

Field of the Invention

The present invention relates to a high-intensity focused ultrasound (HIFU) device, which is configured to obtain skin care and anti-aging effects by focusing high-intensity ultrasound energy on a point of a specific region in the skin by a transducer, solidifying tissue in the specific region using high temperature generated at the focal point and regenerating new skin tissue at the solidified tissue, and a method for controlling a transducer moving piezoelectric device used in the HIFU device.

Description of the Related Art

Generally, a treatment of forming a solidification zone in a dermis layer of the skin, producing collagen in the solidification zone, to fill the solidification zone, and, as such, obtaining skin care effects such as removal of wrinkles is being greatly highlighted. As such a treatment, an invasive method using a microneedle or the like and a non-invasive method using ultrasound or the like are typically used.

For non-invasive treatment, ultrasound is widely used. A medical appliance using high-intensity focused ultrasound (HIFU), which is called an "HIFU device", has recently been highlighted. For example, such an HIFU device may radiate high-density focused ultrasound into tissue of the skin and, as such, may perform a treatment for skin care such as face lifting or skin tightening in a non-invasive manner.

In most cases, HIFU devices generally and widely used for skin care have common basic configurations. FIG. 1 shows the configuration of a handpiece included in a conventional HIFU device.

The handpiece of the conventional HIFU device shown in FIG. 1 includes a handpiece body 10, and a cartridge 20 as a disposable product detachably coupled to the handpiece body 10.

A transducer 25, which receives ultrasound energy and focuses the received ultrasound energy on a point apart therefrom by a focal distance, is provided at the cartridge 20. A driver including components designated by reference numerals 11, etc. should also be provided to linearly move the transducer 25. In a state in which the cartridge 20 is in contact with the skin, focused ultrasound may be uniformly irradiated onto the contact portion of the skin in accordance with linear movement of the transducer 25 and, as such, a thermal solidification point may be formed in the skin.

As shown in FIG. 1, the driver includes components provided at the handpiece body 10, that is, a linear motor 11 and a driving shaft 12. The driver also includes components provided at the cartridge 20, that is, a connecting shaft 21 connected to the motor driving shaft 12 by magnets 13 or the like, a fixed member 23 fixed to the connecting shaft 21, and a transducer fixing member 24 for fixing the transducer 25 to the fixed member 23.

The cartridge 20 is not configured to be permanently used after coupling thereof, but is configured to be disposed after a certain number of treatment times and, as such, to be replaceable with a new one (furthermore, the focal length of the transducer provided at the cartridge is fixed and, as such, various kinds of cartridges having different focal lengths should be prepared as replaceable cartridges). For this reason, only under the condition that the connecting shaft 21 in the cartridge 20 is connected to the driving shaft 12 in the handpiece body 10 by the magnets 13 or a separate connecting means, can the connecting shaft 21 receive driving force of the linear motor 11, to move the transducer 25.

Meanwhile, the cartridge 20 should be filled with certain liquid in order to enable ultrasound radiation of the transducer 25. In connection with this, a bellows 22 should be separately provided to isolate a power transmission including the connecting shaft 21, etc. in the cartridge 20 from the liquid.

As mentioned above, the conventional HIFU device does not employ a system in which the motor directly drives the transducer disposed in the cartridge, but employs a system in which the motor disposed in the handpiece body indirectly drives the transducer disposed in the cartridge. Although a DC motor or a stepper motor is typically used as a linear motor for accurate control of the transducer, such a motor has a great size and, as such, the cartridge should also have a great size for accommodation of the motor. Furthermore, when the cartridge is scrapped, the motor is scrapped together with the cartridge. With regard to this, the direct drive system in which the motor is disposed in the cartridge is impractical.

However, the above-mentioned configuration of the conventional HIFU device uses the system in which the motor provided at the handpiece body indirectly drives the connecting shaft provided at the cartridge and, as such, may have problems of degraded control accuracy and low stability, as compared to the direct drive system.

Furthermore, since the linear motor moves the driving shaft of the motor forwards and rearwards, spaces for movement of the driving shaft should be secured at front and rear sides of the linear motor. For this reason, it is necessary to increase the length or size of the handpiece body and, as such, there may be a problem of a great limitation as to compactness.

In addition, it is necessary to suppress evaporation of moisture as much as possible under the condition that the cartridge is filled with liquid. In the cartridge of the above-mentioned conventional HIFU device, however, considerable moisture loss through the bellows occurs because the cartridge should be provided with the power transmission including the connecting shaft to be connected to the driving shaft of the motor disposed in the handpiece body, etc. As a result, there may be a problem in that a separate sealing structure or means should be provided.

As prior art literature associated with the above-mentioned conventional HIFU device, there are Korean Patent Application Nos. 10-2015-0026533, 10-2017-0013457, and 10-2016-0003984.

SUMMARY OF THE INVENTION

Therefore, the present invention has been made in view of the above problems, and it is an object of the present invention to provide a high-intensity focused ultrasound (HIFU) device capable of achieving accurate and stable control as to movement of a transducer and a treatment position by use of a transducer moving piezoelectric device configured to have a compact size in accordance with a great reduction in the size of a handpiece, and a method for controlling the transducer moving piezoelectric device.

In accordance with one aspect of the present invention, the above and other objects can be accomplished by the provision of a method for controlling a transducer moving piezoelectric device to linearly move a transducer disposed in a cartridge of a high-intensity focused ultrasound handpiece, including: transmitting a high frequency signal to a piezoelectric motor, thereby causing the piezoelectric motor to generate piezoelectric ultrasound, and causing a piezoelectric vibrating shaft connected to the piezoelectric motor to generate vibration in accordance with the piezoelectric ultrasound, coupling a piezoelectric vibrated mover provided with the transducer to the piezoelectric vibrating shaft, thereby causing the piezoelectric vibrated mover to move along the piezoelectric vibrating shaft in accordance with the vibration of the piezoelectric vibrating shaft, and predetermining information as to positions, at which the transducer radiates ultrasound, and performing a control operation for stopping the movement of the piezoelectric vibrated mover along the piezoelectric vibrating shaft when it is sensed that the piezoelectric vibrated mover reaches one of the predetermined position, and irradiating ultrasound through the transducer.

The control operation for stopping the piezoelectric vibrated mover and irradiating ultrasound through the transducer may include previously storing, in association with a position sensor to sense a position of the piezoelectric vibrated mover, sensing values respectively corresponding to a plurality of positions, at which the transducer radiates ultrasound, stopping an operation of the piezoelectric motor to stop the piezoelectric vibrated mover and controlling the transducer to radiate ultrasound when a sensed value of the position sensor generated during movement of the piezoelectric vibrated mover is equal to one of the stored sensing values, and repeating the vibration generation, the movement of the piezoelectric vibrated mover along the piezoelectric vibrating shaft, and the ultrasound irradiation through the transducer so that the transducer sequentially radiates ultrasound at the positions respectively corresponding to the stored sensing values.

A magnet may be provided at an end of the piezoelectric vibrated mover, and a plurality of Hall sensors may be disposed in the cartridge, to sense a magnetic field of the magnet. In this case, the control operation for stopping the piezoelectric vibrated mover and irradiating ultrasound through the transducer may include previously storing, in association with the Hall sensors, sensing values respectively corresponding to a plurality of positions, at which the transducer radiates ultrasound, stopping an operation of the piezoelectric motor to stop the piezoelectric vibrated mover and controlling the transducer to radiate ultrasound when one of sensed values of the Hall sensors generated during movement of the piezoelectric vibrated mover is equal to one of the stored sensing values, and repeating the vibration generation, the movement of the piezoelectric vibrated mover along the piezoelectric vibrating shaft, and the ultrasound irradiation through the transducer so that the transducer sequentially radiates ultrasound at the positions respectively corresponding to the stored sensing values.

The method may further include moving the piezoelectric vibrated mover for a predetermined time after irradiation of ultrasound through the transducer at a last one of the predetermined positions, moving the piezoelectric vibrated mover in an opposite direction, and performing a control operation for stopping the movement of the piezoelectric vibrated mover along the piezoelectric vibrating shaft when it is sensed that the piezoelectric vibrated mover reaches one of the predetermined positions, and irradiating ultrasound through the transducer, whereby a double shot of ultrasound is carried out at a treatment area through the transducer.

In accordance with another aspect of the present invention, there is provided a method for controlling a transducer moving piezoelectric device to linearly move a transducer disposed in a cartridge of a high-intensity focused ultrasound handpiece, including transmitting a high frequency signal to a piezoelectric motor, thereby causing the piezoelectric motor to generate piezoelectric ultrasound, and causing a piezoelectric vibrating shaft connected to the piezoelectric motor to generate vibration in accordance with the piezoelectric ultrasound, coupling a piezoelectric vibrated mover provided with the transducer to the piezoelectric vibrating shaft, thereby causing the piezoelectric vibrated mover to move along the piezoelectric vibrating shaft in accordance with the vibration of the piezoelectric vibrating shaft, and performing a control operation for sensing light emission or light reception at positions where the transducer radiates ultrasound, controlling the piezoelectric vibrated mover to stop upon sensing the light emission or the light reception during movement thereof along the piezoelectric vibrating shaft, and controlling the transducer to radiate ultrasound.

In accordance with another aspect of the present invention, there is provided a high-intensity focused ultrasound device for controlling a transducer disposed in a cartridge to linearly move and to radiate ultrasound for treatment, including a transducer moving piezoelectric device including a piezoelectric motor disposed in the cartridge, to generate piezoelectric ultrasound in accordance with a high frequency signal, a piezoelectric vibrating shaft connected to the piezoelectric motor, to generate vibration in accordance with the piezoelectric ultrasound, and a piezoelectric vibrated mover provided with the transducer and coupled to the piezoelectric vibrating shaft, to move along the piezoelectric vibrating shaft in accordance with the vibration of the piezoelectric vibrating shaft, a position sensor for sensing a position of the piezoelectric vibrated mover, a high frequency generator for generating a high frequency signal enabling the piezoelectric motor to generate piezoelectric ultrasound and a high frequency signal enabling the transducer to radiate ultrasound for treatment, and a controller for predetermining information as to positions, at which the transducer radiates ultrasound, and controlling the high frequency generator performing a control operation for stopping the movement of the piezoelectric vibrated mover along the piezoelectric vibrating shaft when it is sensed that the piezoelectric vibrated mover reaches one of the predetermined positions, and irradiating ultrasound through the transducer.

The controller may previously store, in association with the position sensor, sensing values respectively corresponding to a plurality of positions, at which the transducer radiates ultrasound, and may control the high frequency generator such that the piezoelectric motor stops and the transducer radiates ultrasound when a sensed value of the position sensor generated during movement of the piezoelectric vibrated mover is equal to one of the stored sensing values.

A magnet may be provided at an end of the piezoelectric vibrated mover, and a plurality of Hall sensors may be disposed at an area facing the magnet in a movement path of the piezoelectric vibrated mover within the cartridge while being spaced apart from one another by a predetermined distance. In this case, the controller may previously store, in association with the Hall sensors, sensing values respectively corresponding to a plurality of positions, at which the transducer radiates ultrasound, stops an operation of the piezoelectric motor to stop the piezoelectric vibrated mover and controls the transducer to radiate ultrasound when one of sensed values of the Hall sensors generated during movement of the piezoelectric vibrated mover is equal to one of the stored sensing values.

The position sensor may include an optical sensor installed at one side of the transducer moving piezoelectric device, to emit light toward the piezoelectric vibrated mover, to receive the light reflected after being emitted, and to compare the received light with the emitted light, thereby sensing the position of the piezoelectric vibrated mover.

In accordance with another aspect of the present invention, there is provided a high-intensity focused ultrasound device for controlling a transducer disposed in a cartridge to linearly move and to radiate ultrasound for treatment, including a transducer moving piezoelectric device including a piezoelectric motor disposed in the cartridge, to generate piezoelectric ultrasound in accordance with a high frequency signal, a piezoelectric vibrating shaft connected to the piezoelectric motor, to generate vibration in accordance with the piezoelectric ultrasound, and a piezoelectric vibrated mover provided with the transducer and coupled to the piezoelectric vibrating shaft, to move along the piezoelectric vibrating shaft in accordance with the vibration of the piezoelectric vibrating shaft, a high frequency generator for generating a high frequency signal enabling the piezoelectric motor to generate piezoelectric ultrasound and a high frequency signal enabling the transducer to radiate ultrasound for treatment, an optical element array unit including a first optical element provided at one side of the piezoelectric vibrated mover, the first optical element being one of a light emitting element and a light receiving element, and an optical element array provided at an area facing the first optical element, the optical element array including a plurality of second optical elements each being the other of the light emitting element and the light receiving element, so that light reception is achieved between the first optical element and the second optical elements during movement of the piezoelectric vibrated mover along the piezoelectric vibrating shaft, and a controller for controlling the high frequency generator to enable the piezoelectric vibrated mover to move in accordance with vibration generated by the piezoelectric ultrasound and to enable the transducer to radiate ultrasound, stopping the piezoelectric vibrated mover when the light reception is achieved by the optical element array device, and irradiating ultrasound through the transducer.

In accordance with another aspect of the present invention, there is provided a high-intensity focused ultrasound device for controlling a transducer disposed in a cartridge to linearly move and to radiate ultrasound for treatment, including a transducer moving piezoelectric device including a piezoelectric motor disposed in the cartridge, to generate piezoelectric ultrasound in accordance with a high frequency signal, a piezoelectric vibrating shaft connected to the piezoelectric motor, to generate vibration in accordance with the piezoelectric ultrasound, and a piezoelectric vibrated mover provided with the transducer and coupled to the piezoelectric vibrating shaft, to move along the piezoelectric vibrating shaft in accordance with the vibration of the piezoelectric vibrating shaft, a high frequency generator for generating a high frequency signal enabling the piezoelectric motor to generate piezoelectric ultrasound and a high frequency signal enabling the transducer to radiate ultrasound for treatment, a light receiving sensor provided at one side of the piezoelectric vibrated mover, an optical slit unit including a sensor housing extending along a movement path of the piezoelectric vibrated mover, a light source disposed in the sensor housing, and slits formed at positions of the sensor housing corresponding to positions, at which the transducer radiates ultrasound, respectively, to allow light emitted from the light source to pass therethrough, and a controller for controlling the high frequency generator to enable the piezoelectric vibrated mover to move in accordance with vibration generated by the piezoelectric ultrasound and to enable the transducer to radiate ultrasound, stopping the piezoelectric vibrated mover when the light receiving sensor receives light passing through one of the slits of the optical slit unit, and irradiating ultrasound through the transducer.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Hereinafter, concrete contents of a high-intensity focused ultrasound (HIFU) device according to the present invention and a method for controlling a transducer moving piezoelectric device used in the HIFU device in accordance with the present invention will be described with reference to the accompanying drawings.

Figure 1:
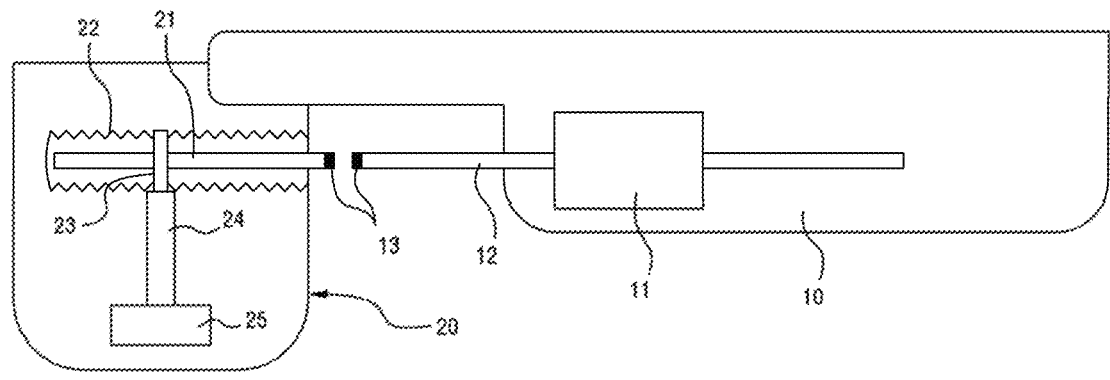
FIG. 1 is a view showing a configuration of a conventional high-intensity focused ultrasound (HIFU) device.
Figure 2A:
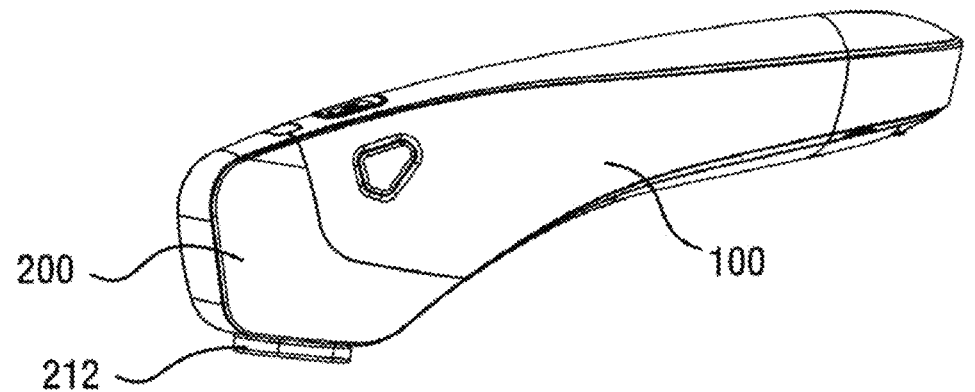
FIGS. 2A and 2B are perspective views illustrating the HIFU device according to an embodiment of the present invention.
Figure 2B:
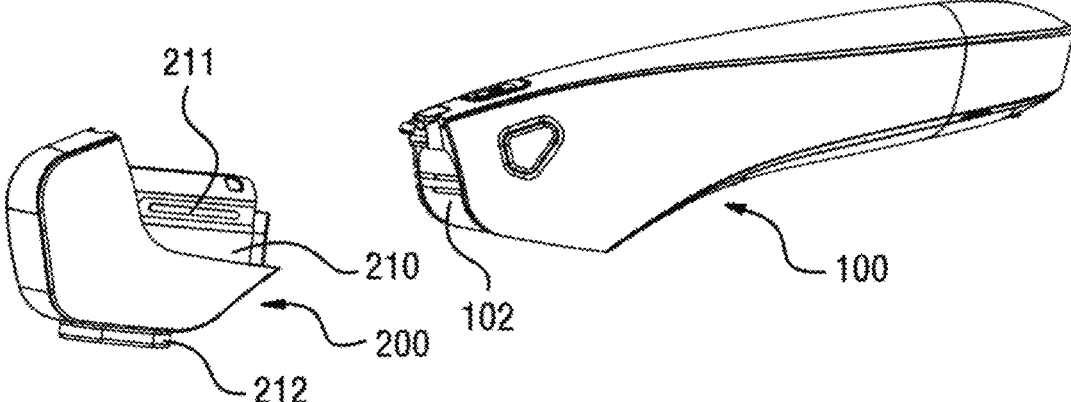
Figure 3:
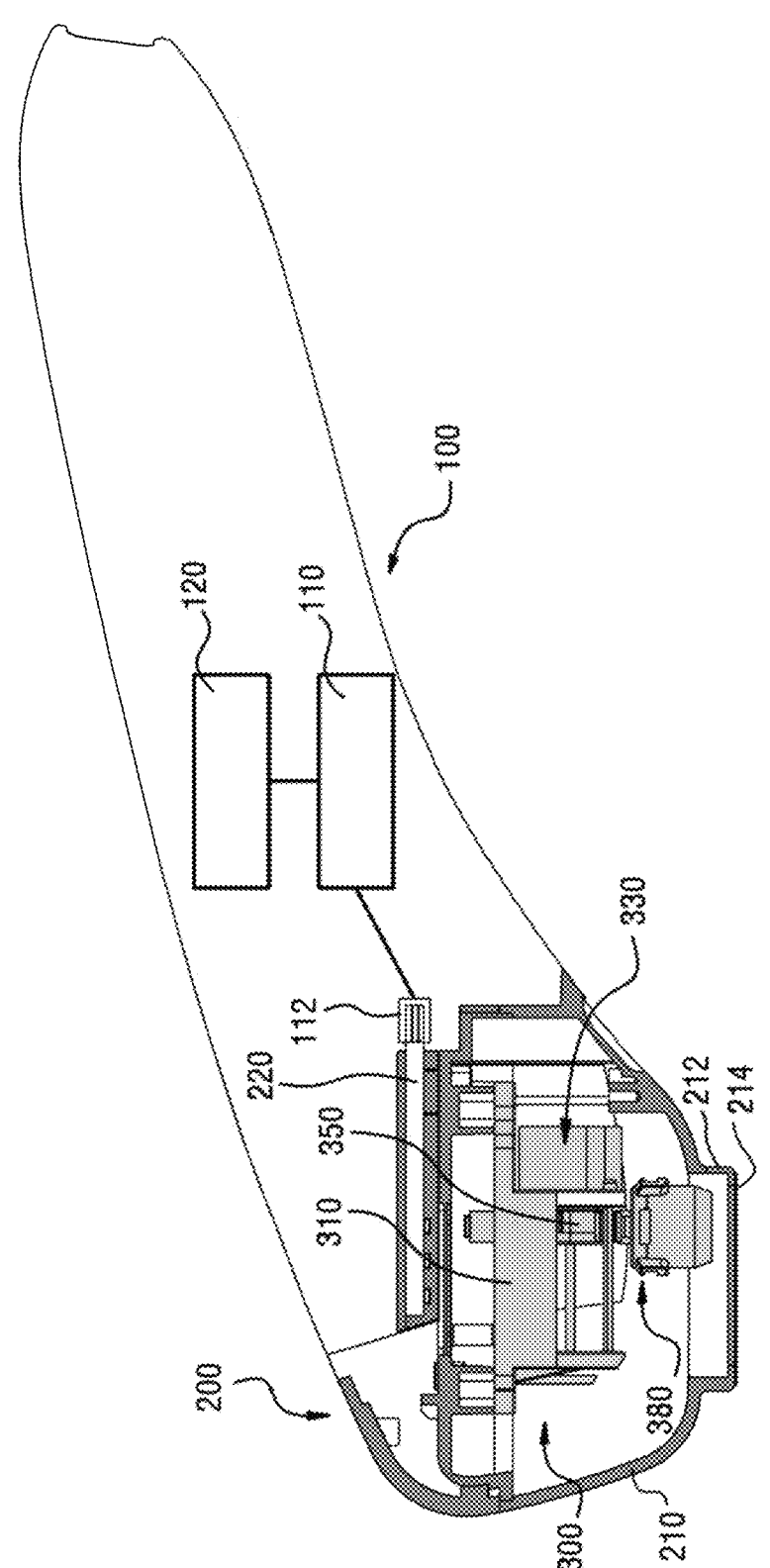
FIG. 3 is a schematic view illustrating an inner configuration of the HIFU device illustrated in FIGS. 2A and 2B.

First, an HIFU device according to an embodiment of the present invention will be described with reference to FIGS. 2A, 2B and 3. FIGS. 2A and 2B are perspective views of the HIFU device according to the illustrated embodiment of the present invention. FIG. 3 is a schematic view illustrating an inner configuration of the HIFU device illustrated in FIGS. 2A and 2B.

As illustrated in FIGS. 2A, 2B and 3, the HIFU device according to the illustrated embodiment of the present invention includes a handpiece body 100, a cartridge 200, and a piezoelectric driver (300) disposed in the cartridge 200.

FIG. 2A shows a state of the HIFU device according to the illustrated embodiment in which the cartridge 200 is coupled to the handpiece body 100. FIG. 2B shows a state in which the cartridge 200 is separated from the handpiece body 100.

The HIFU device may be configured to be connected to a separate appliance body (not shown) in a wired manner and to operate in a wireless manner without being connected to the separate appliance body.

In FIGS. 2A and 2B, reference numeral "212" designates a contact head which is a portion of the cartridge 200 to contact the skin of a person to be treated (hereinafter simply referred to as a "patient"), reference numeral "210" designates a body of the cartridge 200, reference numeral "211" designates a handpiece coupling section, and reference numeral "102" designates a cartridge coupling section.

As illustrated in FIGS. 2A and 2B, when the handpiece coupling section 211, which is provided at the cartridge body 210 of the cartridge 200, is coupled to the cartridge coupling section 102, which is provided at a front portion of the handpiece body 100, a printed circuit board (PCB) provided at the cartridge 200 is electrically connected to a controller provided at the handpiece body 100 and, as such, a transducer disposed in the cartridge 200 may perform irradiation with ultrasound while moving under control of the controller.

The HIFU device according to the illustrated embodiment of the present invention has no connection configuration, except for electrical connection between the cartridge 200 and the handpiece body 100. That is, in the HIFU device, there is no power connection configuration as in the configuration of the conventional HIFU device in which the shaft of the cartridge is connected to the driving shaft of the driving device.

As illustrated in FIG. 3, the handpiece body 100 includes an ultrasound generator 120 disposed in the handpiece body

100, and a controller 110 disposed in the handpiece body 100, to control generation of an ultrasound signal from the ultrasound generator 120.

In the HIFU device according to the present invention, constituent components such as a linear motor and a motor driving shaft are not disposed in the handpiece body 100 and, as such, considerable extra space may be secured in the handpiece body 100. Accordingly, the ultrasound generator 120 and the controller 110 for controlling the ultrasound generator 120, which are difficult to provide at the handpiece of the conventional HIFU device (thus, inevitably being provided at the body) may be installed in the handpiece body 100, and, as such, the HIFU device according to the present invention has a feature in that the size of the body may be greatly reduced or the appliance body itself may be eliminated, and, at the same time, the handpiece may be further compacted.

Figure 4:
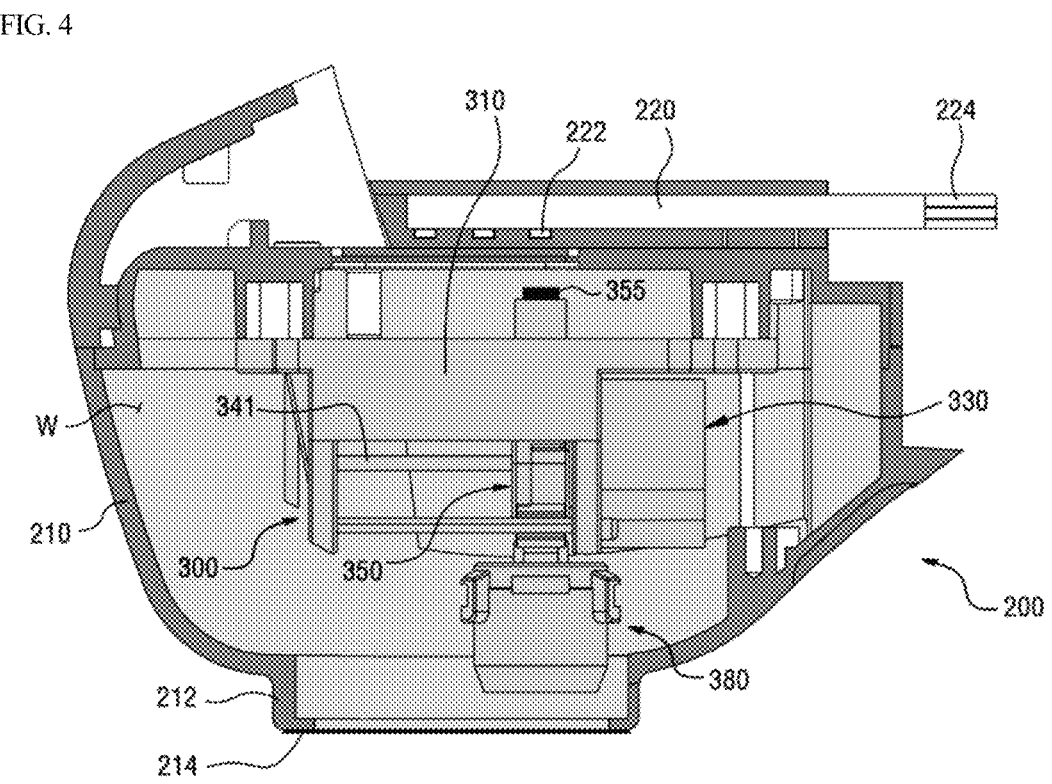
FIG. 4 is an enlarged view illustrating a cartridge of the HIFU device according to the embodiment of the present invention illustrated in FIG. 3.

Hereinafter, more concrete configurations of the above-described cartridge and transducer moving piezoelectric device will be described with reference to FIG. 4. FIG. 4 shows, in an enlarged state, the cartridge of the HIFU device according to the embodiment of the present invention illustrated in FIG. 3.

As illustrated in FIG. 4, the cartridge 200 of the HIFU device according to the illustrated embodiment of the present invention includes the cartridge body 210, which is filled with a fluid W for generation of ultrasound, and the contact head 212, which is to closely contact the skin of a patient. The contact head 212 is disposed at one side of the cartridge body 210. The cartridge 200 also includes a PCB 220 disposed at an outer surface of the cartridge body 210.

The transducer moving piezoelectric device 300, which functions as a driving means for driving a transducer 380, to move the transducer 380, is disposed in the cartridge body 210, together with the transducer 380. The transducer moving piezoelectric device 300 and the transducer 380 are dipped in the fluid W filling the cartridge body 210.

The cartridge body 210 is configured to substantially completely seal the interior thereof in order to prevent the fluid W from being lost due to evaporation or the like. In connection with this, the cartridge of the conventional HIFU device has a configuration in which fluid loss may easily occur, because the cartridge has a power connection configuration to be connected to the motor provided at the handpiece body. On the contrary, the cartridge 200 of the HIFU device according to the illustrated embodiment of the present invention has a feature in that the interior of the cartridge 200 is substantially completely sealed and, as such, there is no or little substantial fluid loss of the cartridge 200.

As illustrated in FIG. 4, the transducer moving piezoelectric device according to the illustrated embodiment of the present invention uses a piezoelectric motor as a driving unit in order to enable the transducer moving piezoelectric device to operate in a state of being dipped in the fluid W contained in the cartridge body 210.

The piezoelectric motor has an advantage in that the piezoelectric motor uses a considerably low driving voltage, as compared to conventional linear motors or DC motors, while being manufactured to have a very small size.

Such a piezoelectric motor has also been used in conventional cases. However, the inventors have developed a transducer moving piezoelectric device capable of exhibiting suitable performance in an HIFU device through use of a piezoelectric motor, after conducting active research into application of a piezoelectric motor to an HIFU device. The present invention provides a transducer moving piezoelectric device capable of accurately controlling movement of a transducer through an operation according to driving force of a piezoelectric motor, even though the transducer moving piezoelectric device is dipped in a fluid contained in a cartridge body.

As illustrated in FIGS. 3 and 4, the transducer moving piezoelectric device 300 includes a driving frame 310 fixed to one side of the cartridge body 210 within the cartridge body 210, a piezoelectric driving unit 330 for generating driving force using ultrasound generated in accordance with a high frequency signal from the high frequency generator 120, and a piezoelectric vibrated mover 350 for moving the transducer 380 while being moved by the driving force generated from the piezoelectric driving unit 330.

The piezoelectric vibrated mover 350, to which the transducer 380 is coupled, moves along a piezoelectric vibrating shaft 341 of the piezoelectric driving unit 330 in accordance with vibration of the piezoelectric vibrating shaft 341.

A concrete configuration of the transducer moving piezoelectric device 300 will be described later.

Meanwhile, the above-described transducer moving piezoelectric device 300 is configured to be driven in the fluid W contained in the cartridge body 210, as illustrated in FIGS. 3 and 4. In connection with this, the cartridge body 210 is configured to be substantially sealed in order to prevent loss of the fluid W contained therein.

As illustrated in FIG. 4, the PCB 220 is disposed at an outer top surface of the cartridge body 210. The connector 224 is provided at an exposed end of the PCB 220. When the cartridge 200 is coupled to the handpiece body 100, the connector 224 is coupled to a contact 112 provided at the handpiece body 100 and, as such, electrical connection may be achieved.

As illustrated in FIGS. 3 and 4, the transducer moving piezoelectric device 300 is disposed in the cartridge body 210 in a fixed state. The PCB 220, which is disposed adjacent to the transducer moving piezoelectric device 300 outside the cartridge body 210, is electrically connected to the transducer moving piezoelectric device 300 via electric wires. In this case, the electric wires may be treated by a sealing process in order to maintain the interior of the cartridge body 210 in a sealed state.

The piezoelectric driving unit 330 of the transducer moving piezoelectric device 300 and the transducer 380 are electrically connected to the PCB 220 by sealed electric wires and, as such, are connected to the controller 110 disposed in the handpiece body 100 when the connector 224 is connected to the contact 112 in accordance with coupling of the cartridge 200 to the handpiece body 100. In this state, the controller 110 may transmit a high frequency signal for generation of high-intensity focused ultrasound to be irradiated by the transducer 380 and a high frequency signal for generation of ultrasound vibration as driving force of the piezoelectric driving unit 330 while controlling the high frequency generator 120. The PCB 220 may transfer respective signals to the transducer 380 and the piezoelectric driving unit 330 via associated ones of the electric wires.

As high frequency signals generated from the high frequency generator 120 are transmitted to the transducer 380 and the piezoelectric driving unit 330, respectively, under control of the controller 110, as described above, the transducer 380 transmits ultrasound energy to a specific position in the skin through radiation of high-intensity focused ultrasound according to a focal length of a piezoelectric ceramic disposed in the transducer 380, and, at the same time, the piezoelectric driving unit 330 generates ultrasound vibration in accordance with the associated high frequency signal and, as such, moves the piezoelectric vibrated mover 350, thereby causing the transducer 380 to move.

In this case, the contact head 212 of the cartridge 200 is open at a bottom portion thereof, and the open portion is sealed by a film 214 made of a specific material. When the skin of a patient is subjected to ultrasound treatment, ultrasound energy radiated through the transducer 380 passes through the film 214 under the condition that the portion of the contact head 212 corresponding to the film 214 is in contact with the skin, and is then transferred to tissue present at a focal distance in the skin.

Meanwhile, as illustrated in FIG. 4, the magnet 355 is fixed to an end of the piezoelectric vibrated mover 350 in the transducer moving piezoelectric device 300, and magnetic field sensors such as the Hall sensors 222 provided at the PCB 220 are arranged in plural at an area facing the magnet 355 while being uniformly spaced apart from one another by a predetermined distance. As the piezoelectric vibrated mover 350 moves the transducer 380 in accordance with driving force of the piezoelectric driving unit 330, the magnet 355 moves. At this time, the Hall sensors 222 on the PCB 220 sense a magnetic field of the magnet 355 and, as such, sense and trace movement of the piezoelectric vibrated mover 350, that is, movement of the transducer 380 (a signal sensed by each Hall sensor 222 is transmitted to the controller 110 and, as such, the controller 110 obtains information as to sensed and traced movement of the transducer 380, and controls generation of a high frequency signal based on the obtained information).

Meanwhile, a concrete configuration of the transducer moving piezoelectric device 300 according to the illustrated embodiment of the present invention will be described with reference to FIGS. 5 to 7.

Figure 5:
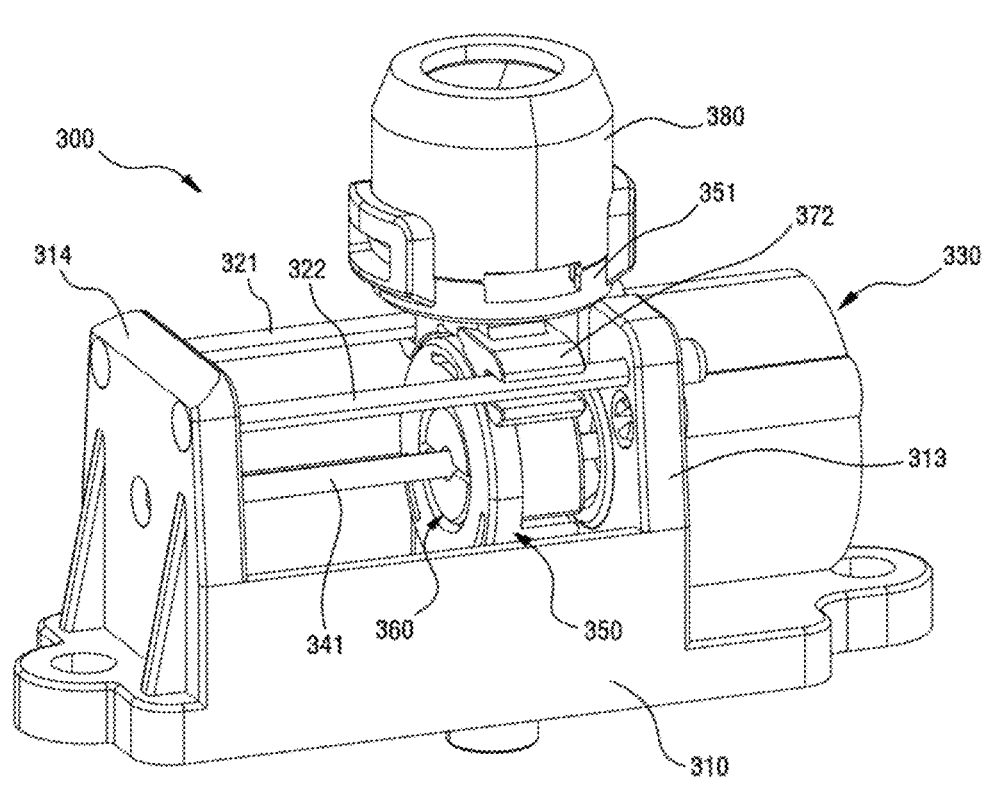
FIG. 5 is a perspective view of the transducer moving piezoelectric device used in the HIFU device according to the illustrated embodiment of the present invention.

FIG. 5 illustrates a perspective view of the transducer moving piezoelectric device 300 according to the illustrated embodiment of the present invention. FIG. 6 illustrates an exploded perspective view of the transducer moving piezoelectric device illustrated in FIG. 5. FIG. 7 illustrates an exploded perspective view of the piezoelectric vibrated mover illustrated in FIG. 6.

Figure 6:
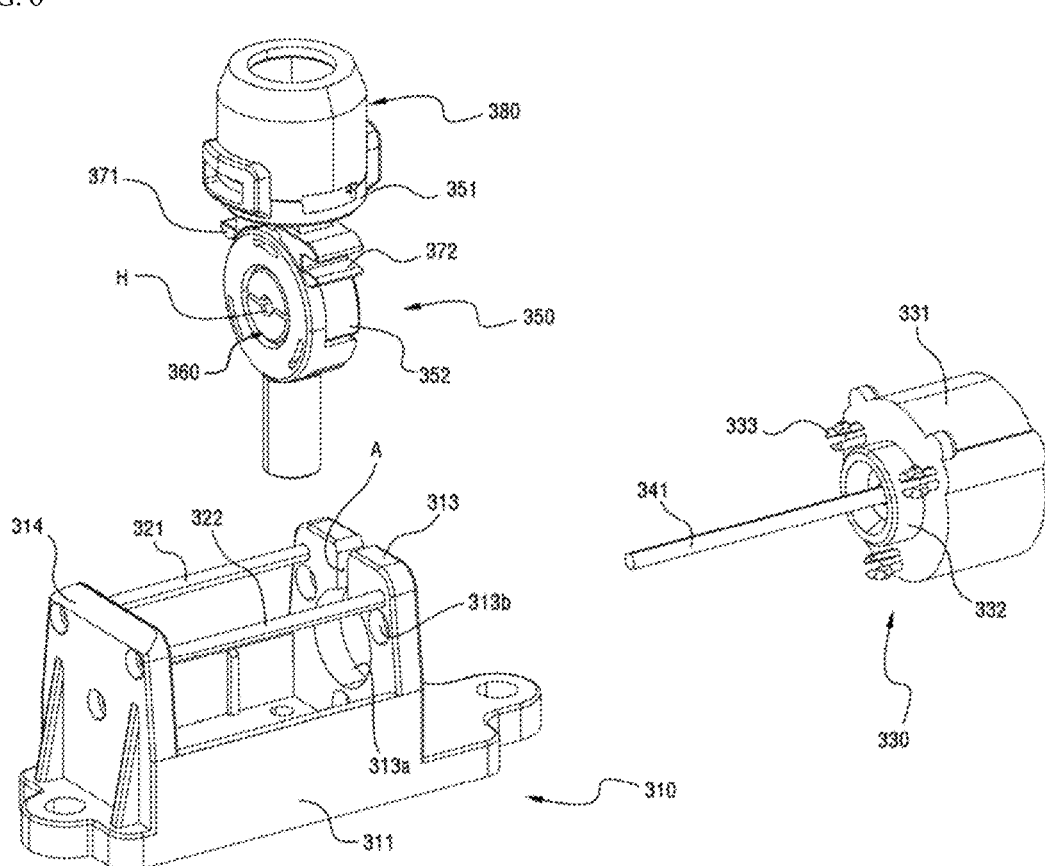
FIG. 6 is an exploded perspective view of the transducer moving piezoelectric device illustrated in FIG. 5.

As illustrated in FIGS. 5 and 6, the transducer moving piezoelectric device 300 according to the illustrated embodiment of the present invention may include the driving frame 310, the piezoelectric driving unit 330, and the piezoelectric vibrated mover 350.

As illustrated in FIGS. 5 and 6, the driving frame 310 may include a frame body 311, a driving unit coupling/support member 313 provided at one side of the frame body 311, and an operation support member 314 provided at the other side of the frame body 311. The driving frame 310 may also include first and second guide shafts 321 and 322, each of which has one end fixed to the driving unit coupling/support member 313 and the other end fixed to the operation support member 314.

As illustrated in FIG. 6, a body coupling hole 313a and engagement holes 313b may be provided at the driving unit coupling/support member 313. The piezoelectric driving unit 330 is primarily coupled to the body coupling hole 313a, and is secondarily engaged with the engagement holes 313b. Accordingly, the piezoelectric driving unit 330 may be firmly coupled to the driving unit coupling/support member 313.

Meanwhile, as illustrated in FIGS. 5 and 6, the piezoelectric driving member 330 includes a piezoelectric motor (not shown) for generating piezoelectric ultrasound in accordance with a high frequency signal from the ultrasound generator 120 (FIG. 3) provided at the handpiece body, and a driving unit coupling body 331 coupled to the driving unit coupling/support member 313 while accommodating the piezoelectric motor. The piezoelectric motor is received in the driving unit coupling body 331 and, as such, is not visible in FIGS. 5 and 6.

As the piezoelectric motor of the piezoelectric driving unit 330 generates ultrasound vibration in a state in which the piezoelectric driving unit 330 is coupled to the driving unit coupling/support member 313, the vibration is transmitted to the entirety of the driving frame 310. In connection with this, an intermediate space A is formed at a portion of the driving unit coupling/support member 313, to more or less attenuate vibration transmitted to the entirety of the driving frame 310. It may also be possible to more or less absorb vibration transmitted to the driving frame 310 by providing a member made of a vibration absorbing material at the intermediate space A.

The piezoelectric motor disposed in the driving unit coupling body 331 may be provided with a piezoelectric vibrating shaft 314. The piezoelectric vibrating shaft 314 is connected, at one end thereof, to the piezoelectric motor and, as such, generates vibration in accordance with piezoelectric ultrasound from the piezoelectric motor. When the driving unit coupling body 331 is coupled to the driving unit coupling/support member 313, the other end of the piezoelectric vibrating shaft 314 is fixed to the operation support member 314.

A body coupling portion 332 and slide-fit engagement portions 333 are provided at one side of the driving unit coupling body 331. The body coupling portion 332 may be coupled to the body coupling hole 313a of the driving unit coupling/support member 313 in a tight fit manner. At the same time, the slide-fit engagement portions 333 may be firmly engaged with the engagement holes 313b in a slide-fit manner.

Meanwhile, as illustrated in FIGS. 5 and 6, the piezoelectric vibrated mover 350 is coupled to the piezoelectric vibrating shaft 341 such that the piezoelectric vibrated mover 350 is movable along the piezoelectric vibrating shaft 341 in accordance with vibration of the piezoelectric vibrating shaft 341 and, as such, the transducer 380 coupled to the piezoelectric vibrated mover 350 is movable.

Figure 7:
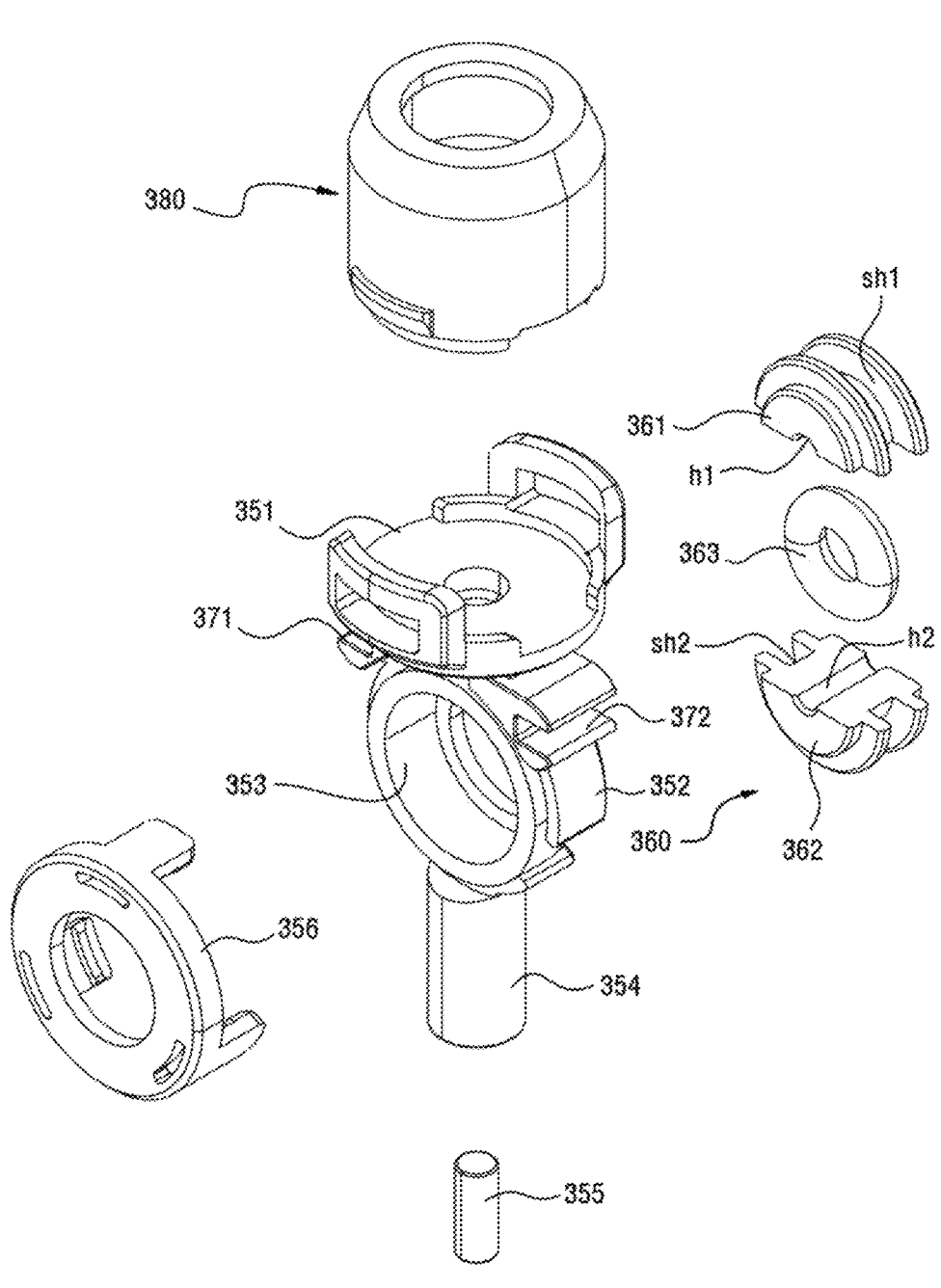
FIG. 7 is an exploded perspective view of a piezoelectric vibrated mover illustrated in FIG. 6'

As illustrated in FIGS. 6 and 7, the piezoelectric vibrated mover 350 may include an operating body 352, a transducer coupling member 351 provided at the operating body 352 and coupled with the transducer 380, and a driving core member 360 surrounding the piezoelectric vibrating shaft 341 while being received in a core receiving portion 353 formed at the operating body 352. The driving core member 360 is movable along the piezoelectric vibrating shaft 341 in accordance with vibration of the piezoelectric vibrating shaft 341.

The transducer coupling member 351 may be disposed at one end of the operating body 352 and, as such, the transducer 380 may be coupled to the operating body 352. A column member 354 may be provided at the other end of the operating body 352, to receive the magnet 355 as described above.

The driving core member 360 disposed in the core receiving portion 353 of the piezoelectric vibrated mover 350 may include a first driving core 361 disposed in one side of the core receiving portion 353 of the operating body 352 and provided with a groove h1 corresponding to the piezoelectric vibrating shaft 341, and a second driving core 362 disposed in the other side of the core receiving portion 353, to face the first driving core 361, and provided with a groove h2 corresponding to the piezoelectric vibrating shaft 341. The driving core member 360 may also include an elastic support ring 363 for elastically supporting a state in which the piezoelectric vibrating shaft 341 is fitted in a hole H formed by the groove h1 of the first driving core 361 and the groove h2 of the second driving core 362.

The first and second driving cores 361 and 362 may be made of specific metal. The piezoelectric vibrating shaft 341 may extend through the hole H formed by the grooves h1 and h2 of the first and second driving cores 361 and 362 without being tightly fitted in the hole H, that is, under the condition in which a micro-gap is formed between the piezoelectric vibrating shaft 341 and the hole H.

As a micro-gap is present between the hole H and the piezoelectric vibrating shaft 341, ultrasound vibration generated from the piezoelectric vibrating shaft 341 is transmitted to the driving core unit 360 and, as such, the piezoelectric vibrated mover 350 may move in accordance with the transmitted vibration.

In this case, movement of the piezoelectric vibrated mover 350 may be adjusted as the frequency of a frequency signal generated from the high frequency generator 120 is controlled by the controller 110 (FIG. 3).

The controller 110 may control the transducer to move at an appropriate speed by appropriately controlling the frequency of the frequency signal in accordance with operation of the user to manipulate the device or sensing of a position of the transducer.

As illustrated in FIG. 7, a first support groove sh1 is formed at the first driving core 361, and a second support groove sh2 is formed at the second driving core 362. The elastic support ring 363 is received in the first and second support grooves sh1 and sh2 under the condition that the first and second driving cores 361 and 362 are in contact with each other to form the hole H and, as such, the elastic support ring 363 elastically supports the contact state of the first and second driving cores 361 and 362.

As elastic support of the first and second driving cores 361 and 362 is achieved by the elastic support ring 363, as described above, vibration of the piezoelectric vibrating shaft 341 may be reliably transmitted to the first and second driving cores 361 and 362 and, as such, the piezoelectric vibrated mover 350 may be easily movable.

In addition, as illustrated in FIG. 7, a core support cover 356 may be provided to support a state in which the driving core unit 360 is received in the core receiving portion 353 of the operating body 352 in the piezoelectric vibrated mover 350. When the core support cover 356 is coupled to the operating body 352 in a state in which the driving core unit 360 is received in the core receiving portion 353, the core support cover 356 supports the received state of the driving core unit 360.

Meanwhile, as illustrated in FIGS. 5 to 7, the transducer moving piezoelectric device according to the illustrated embodiment of the present invention may include a first slide groove 371 provided at one side of the operating body 352 of the piezoelectric vibrated mover 350 and a second slide groove 372 at the other side of the operating body 352. The first slide groove 371 is fitted around the first guide shaft 321, and the second slide groove 372 is fitted around the second guide shaft 372. When the piezoelectric vibrated mover 350 is moved by the piezoelectric vibrating shaft 341 and the driving core unit 360, the piezoelectric vibrated mover 350 is guided by the first guide shaft 321 fitted in the first slide groove 371 and the second guide shaft 322 fitted in the second slide groove 372 and, as such, stable movement of the piezoelectric vibrated mover 350 may be achieved.

If the piezoelectric vibrated mover 350 moves in a state in which the first and second guide shafts 321 and 322 are fitted in holes, respectively, in place of the first and second slide grooves 371 and 372, there may be a problem in that movement of the piezoelectric vibrated mover 350 may be inefficiently carried out due to friction generated between each of the guide shafts 321 and 322 and the associated hole. To this end, in the transducer moving piezoelectric device according to the illustrated embodiment of the present invention, each of the first and second slide grooves 371 and 372 in the piezoelectric vibrated mover 350 is formed to be open at one side and, as such, to substantially have a 90°-rotated U shape. As the guide shafts 321 and 322 are fitted in the first and second slide grooves 371 and 372 formed as described above, respectively, there may be a feature in that movement of the piezoelectric vibrated mover 350 is smoothly and stably guided without friction.

Hereinafter, operation of the transducer moving piezoelectric device having the above-described configuration according to the illustrated embodiment of the present invention and operation of the HIFU device using the transducer moving piezoelectric device will be described with reference to FIG. 8.

The transducer 380 coupled to the transducer moving piezoelectric device 300 disposed in the cartridge 200 is a kernel component of the HIFU device. The focal distance of ultrasound varies in accordance with the curvature and installation position of the piezoelectric ceramic disposed in the transducer 380 and, as such, the treatment depth of the skin tissue (treatment area or position) by the ultrasound varies.

Once the piezoelectric ceramic is installed in the transducer 380, the focal length of the piezoelectric ceramic is fixed and, as such, the treatment depth is fixed. The kind of the piezoelectric ceramic (the curvature of the piezoelectric ceramic) and the installation position of the piezoelectric ceramic are determined in accordance with which one of an SMAS layer, a muscle layer and a dermis layer in the skin is determined as a treatment area. Accordingly, cartridges respectively provided with transducers suitable for different treatment areas are prepared and, as such, a selected one of the cartridges meeting a selected treatment area may be used under the condition that the selected cartridge is coupled to the handpiece body.

Information as to the focal length of the transducer or the treatment depth (information previously determined in accordance with the installation position of the piezoelectric ceramic in the transducer) is stored in a memory (not shown) provided at the PCB 220. Information as to the frequency of a high frequency signal for generation of ultrasound to be radiated through the transducer and information as to the frequency of a high frequency signal for driving of the piezoelectric motor may also be previously stored in the memory.

Accordingly, when the cartridge 200 is coupled to the handpiece body 100, the connector 224 is connected to the contact 112 and, as such, electrical connection between the cartridge 200 and the handpiece body 100 is achieved. In this state, the above-described information stored in the memory of the PCB 220 is transmitted to the controller 110 of the handpiece body 100. Accordingly, the controller 110 controls signals generated from the high frequency generator 120 in accordance with the transmitted information and, as such, controls generation of ultrasound from the transducer 380 and the piezoelectric motor.

When a thermal solidification point is formed at a predetermined depth in accordance with ultrasound energy generated through transmission of a high frequency signal to the transducer 380 under control of the controller 110 under the condition that the contact head 212 of the cartridge 200 is closely in contact with the skin, the controller 110 controls a high frequency signal transmitted to the piezoelectric driving unit 330, to move the piezoelectric vibrated mover 350 and, as such, to move the transducer 380. In accordance with movement of the transducer 380, a thermal solidification point is formed at the next position in the same manner as described above.

In such a manner, a plurality of uniformly spaced thermal solidification points CA is created in a treatment area in the skin tissue and, as such, treatment is completed. Collagen is produced or tightening is achieved at the thermal solidification points during a self-healing procedure after the treatment and, as such, skin lifting effects may be obtained.

Figure 8:
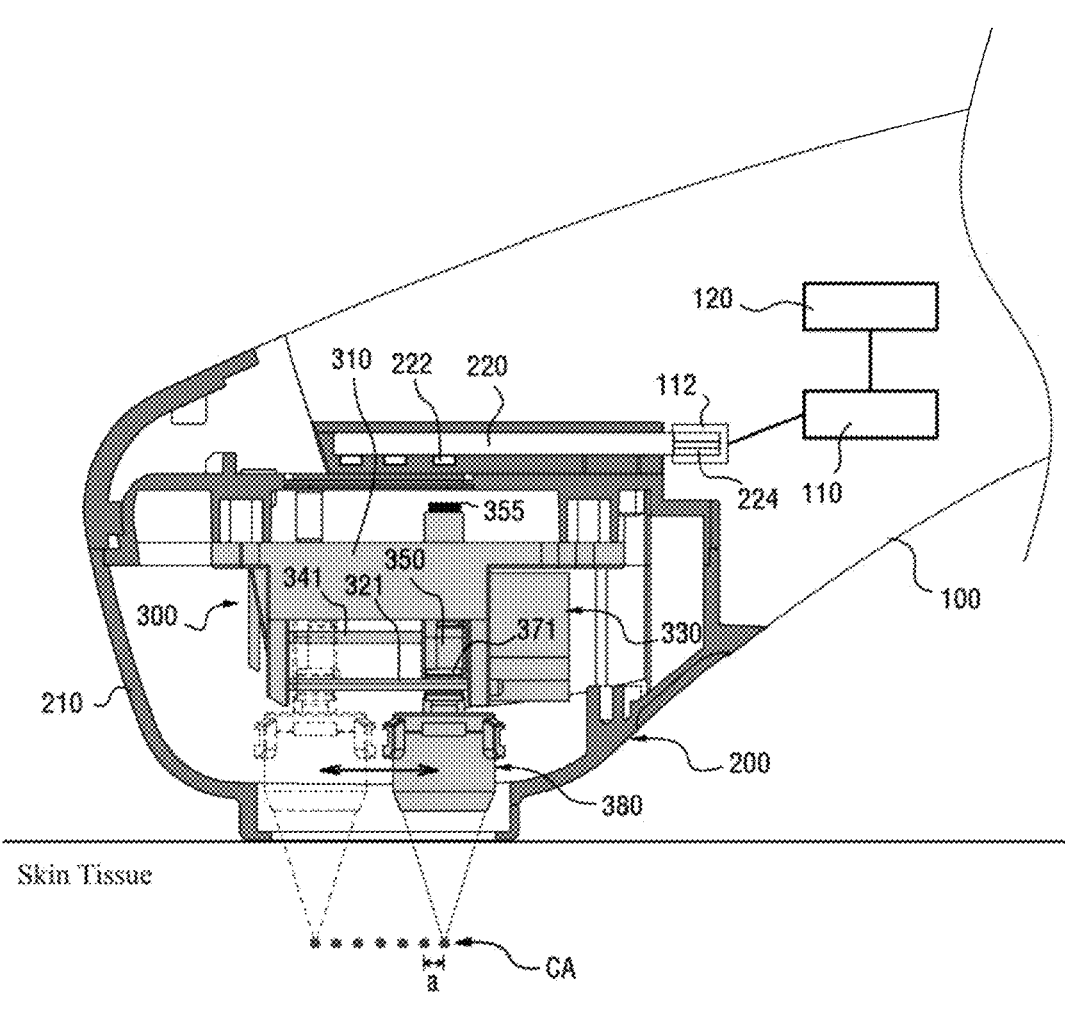
FIG. 8 is a view explaining operation of the HIFU device according to the illustrated embodiment of the present invention.

Meanwhile, as illustrated in FIG. 8, it is necessary to form thermal solidification points CA at a uniform interval a in an area of the skin through radiation of ultrasound by the transducer 380. To this end, the controller 110 controls a high frequency signal generated from the high frequency generator 120, to stop the piezoelectric vibrated mover 350 after moving the piezoelectric vibrated mover 350 by a distance corresponding to the interval a, to form a thermal solidification point through radiation of high-intensity focused ultrasound from the transducer 380 onto a point in the skin corresponding to the focal length of the transducer, to again move the piezoelectric vibrated mover 350 by the distance corresponding to the interval a, and then to repeat the above operations. Thus, a plurality of thermal solidification points CA having a uniform interval a may be formed, as illustrated in FIG. 8.

Hereinafter, a control method for accurately controlling movement of the piezoelectric vibrated mover through the piezoelectric motor of the transducer moving piezoelectric device in order to form a plurality of thermal solidification points having the above-described uniform interval will be described with reference to FIGS. 9 to 12.

FIGS. 9 to 12 illustrate various embodiments associated with the above-described transducer moving piezoelectric device control method. In FIGS. 9 to 12, constituent components are simply illustrated for explanation of control as to movement of the piezoelectric vibrated mover in the transducer moving piezoelectric device.

First, the HIFU device according to the illustrated embodiment and the method for controlling the transducer moving piezoelectric device used in the HIFU device will be described with reference to FIG. 9.

Figure 9:
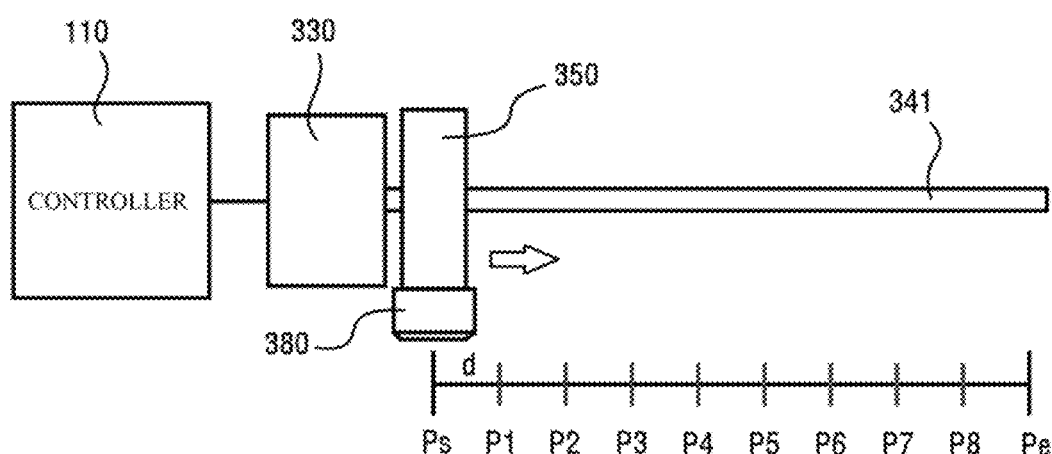
FIG. 9 is a schematic view explaining a method for controlling a piezoelectric vibrated mover and a transducer in a transducer moving piezoelectric device used in the HIFU device in accordance with an embodiment of the present invention.

As illustrated in FIG. 9, in the transducer moving piezoelectric device of the HIFU device according to the illustrated embodiment of the present invention, the piezoelectric motor 330 generates piezoelectric ultrasound under control of the controller 110 and, as such, the piezoelectric vibrating shaft 341 vibrates. In accordance with the vibration, the piezoelectric vibrated mover 350 moves along the piezoelectric vibrating shaft 341 in an arrow direction. The transducer 380 is disposed at an end of the piezoelectric vibrated mover 350 opposite to the magnet 355.

The piezoelectric vibrated mover 350 moves from a start position Ps, and then stops at a position P1. At the position P1, the piezoelectric vibrated mover 350 allows the transducer 380 to irradiate ultrasound onto the skin in order to form a thermal solidification point, and then again moves to a position P2. At the position P2, the piezoelectric vibrated mover 350 allows the transducer 380 to irradiate ultrasound onto the skin in a stopped state, thereby forming another thermal solidification point. In such a manner, the piezoelectric vibrated mover 350 moves up to an arrival position Pe through repeated movement and stops at intervals of a distance d while sequentially allowing the transducer 380 to radiate ultrasound to positions P1 to P8. In this case, the interval of the positions P1 to P8 should be substantially equal to the distance d.

Movement of the piezoelectric vibrated mover 350 at intervals of the distance d as described above may be possible in accordance with control of the frequency and pulses of the high frequency signal transmitted to the piezoelectric motor 330 by the controller 110.

That is, the controller 110 controls the frequency of the high frequency signal transmitted to the piezoelectric motor 330 for movement of the piezoelectric vibrated mover 350 such that the frequency of the high frequency signal becomes constant, and predetermines the number of pulses required for movement of the piezoelectric vibrated mover 350 by the distance d. When the controller 110 applies the predetermined number of pulses to the piezoelectric motor 330, the piezoelectric vibrated mover 350 moves the distance d, and then stops. At this time, the controller 110 transmits a high frequency signal for radiation of ultrasound to the transducer 380, to form a thermal solidification point in an area of the skin. As the above control is repeated, the piezoelectric vibrated mover 350 may stop at each of the positions P1 to P8 after interval movement thereof and may then allow the transducer 380 to radiate ultrasound in the stopped state.

For example, when 120 pulses at a frequency of 50 kHz are applied for movement of the piezoelectric vibrated mover 350 at intervals of the distance d, the controller 110 transmits a signal of 50 kHz and 120 pulses to the piezoelectric motor 330, and then transmits a high frequency signal to the transducer 380 for radiation of ultrasound. As the above operation is repeated, thermal solidification points having a uniform interval may be formed at the positions P1 to P8, respectively. Although FIG. 9 illustrates an example in which the transducer irradiates 8 points P1 to P8 with ultrasound, the present invention is not limited thereto. How many points are to be subjected to irradiation with ultrasound is arbitrary.

Meanwhile, although the same number of pulses is applied, the piezoelectric vibrated mover 350 may not always move the distance d because the piezoelectric motor 330 is connected to one end of the piezoelectric vibrating shaft 341.

For example, although the piezoelectric vibrated mover 350 correctly moves from the position Ps to the position P1 by the distance d in accordance with the signal of 120 pulses, the piezoelectric vibrated mover 350 may not move the distance d in accordance with the signal of 120 pulses when moving from the position P3 to the position P4. In this case, the piezoelectric vibrated mover 350 may not correctly stop at the position P4. Such a phenomenon may become more severe as movement of the piezoelectric vibrated mover 350 is continued.

To this end, numbers of pulses required for respective movements of the piezoelectric vibrated mover 350 among Ps, P1, P2, . . . , P8, and Pe may be measured, and pulse signals having respective measured numbers of pulses may be applied for respective movements of the piezoelectric operation unit 350, and as such, the piezoelectric vibrated mover 350 may accurately move a distance substantially equal to the distance d.

Meanwhile, an HIFU device according to another embodiment of the present invention and a method for controlling a transducer moving piezoelectric device used in the HIFU device will be described with reference to FIG. 10.

The embodiment illustrated in FIG. 9 relates to the method for controlling movement of the piezoelectric vibrated mover in accordance with control of the frequency and pulses of a high frequency signal transmitted to the piezoelectric motor, and, in connection with this, the problem of a difficulty in accurate control has been described.

Figure 10:
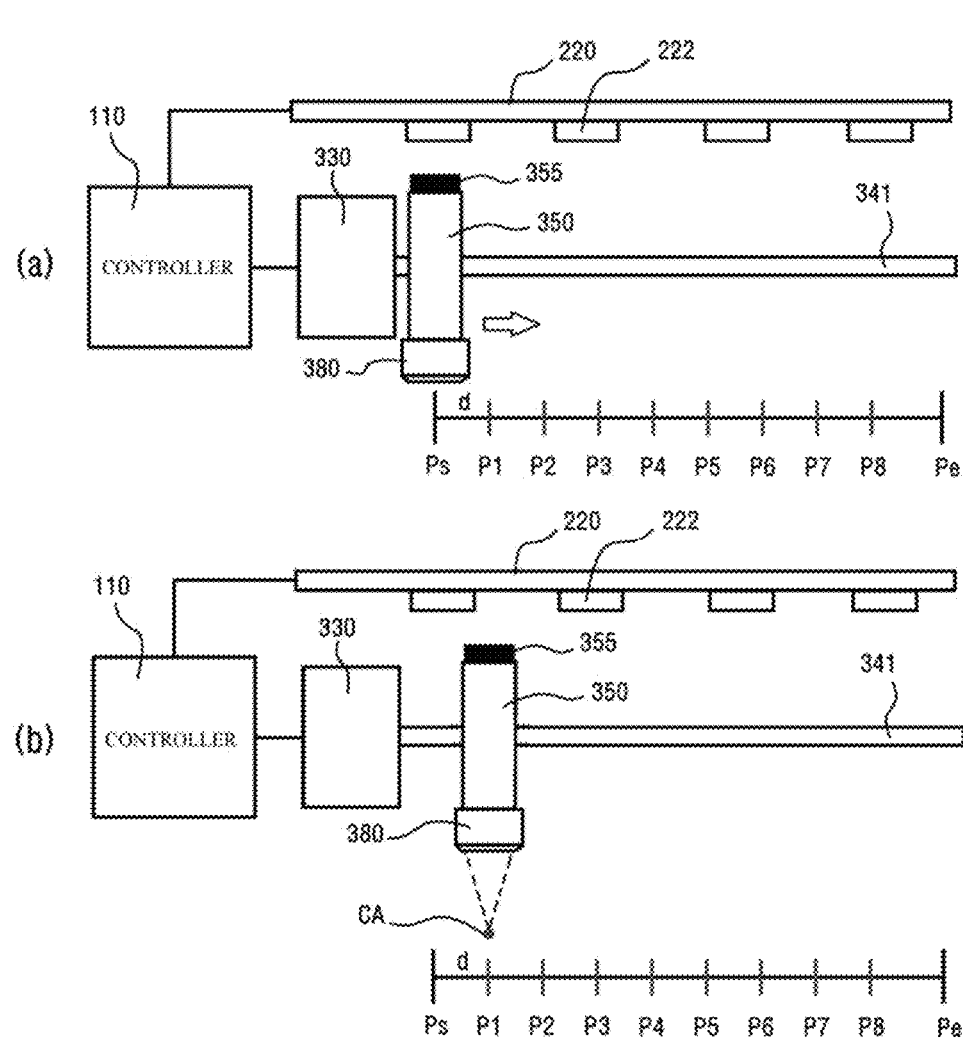
FIGS. 10 to 12 are schematic views explaining methods for controlling a piezoelectric vibrated mover and a transducer in a transducer moving piezoelectric device used in the HIFU device in accordance with various embodiments of the present invention, respectively.

The embodiment illustrated in FIG. 10 provides a control method for more accurate and stable movement of the piezoelectric vibrated mover capable of eliminating the problem encountered in the embodiment illustrated in FIG. 9.

That is, the embodiment illustrated in FIG. 10 provides a control method in which a position of the piezoelectric vibrated mover shifted in accordance with the piezoelectric vibrated mover is sensed by a position sensor provided at the transducer moving piezoelectric device, and, based on a sensed value, the piezoelectric vibrated mover stops at a corresponding one of the positions P1 to P8, and allows radiation of ultrasound at the stopped position.

Matters associated with positions, at which the transducer 380 radiates ultrasound between the start point Ps and the arrival position Pe, that is, P1 to P8, in FIG. 10 are the same as those of FIG. 9, and, as such, no description thereof will be given.

In the control method for the transducer moving piezoelectric device according to this embodiment, the controller 110 performs a control process of: transmitting a high frequency signal to the piezoelectric motor 330 such that the piezoelectric motor 330 generates piezoelectric ultrasound, the piezoelectric vibrating shaft 341 connected to the piezoelectric motor 330 generates vibration according to the generated piezoelectric ultrasound, and the piezoelectric vibrated mover 350 coupled to the piezoelectric vibrating shaft 341 moves along the piezoelectric vibrating shaft 341 in accordance with the vibration of the piezoelectric vibrating shaft 341; predetermining information as to positions P1 to P8, at which the transducer 380 radiates ultrasound; and controlling the piezoelectric vibrated mover 350 and the transducer 380 such that, every time it is sensed that the piezoelectric vibrated mover 350 reaches one of the predetermined positions P1 to P8 after movement thereof along the piezoelectric vibrating shaft 341, the piezoelectric vibrated mover 350 stops, and the transducer 380 is enabled to radiate ultrasound. The movement and stop of the piezoelectric vibrated mover 350 (at the same time, ultrasound radiation through the transducer 380) are repeated from the predetermined position P1 to the predetermined position P8.

Here, the control to stop the piezoelectric vibrated mover and then to irradiate ultrasound through the transducer is a control process in which, in association with the position sensor to sense a position of the piezoelectric vibrated mover 350, the controller 110 predetermines or stores sensing values corresponding to respective positions P1 to P8 and, as such, the controller 110 stops operation of the piezoelectric motor 330 to stop the piezoelectric vibrated mover 350 and controls the transducer 380 to radiate ultrasound when a sensed value of the position sensor generated during movement of the piezoelectric vibrated mover 350 along the piezoelectric vibrating shaft 341 is equal to one of the stored sensing values. The above-described process is repeatedly carried out at the previously stored plural positions P1 to P8.

In more detail, as illustrated in FIG. 10(*a*), in the configuration in which the magnet 355 is provided at an end of the piezoelectric vibrated mover 350, and a plurality of Hall sensors 222 is provided at the PCB 220 disposed in the cartridge, to sense a magnetic field of the magnet 355, sensing values of the Hall sensors 222 at respective positions P1 to P8 are previously stored (the controller may store Information as to the sensing values therein or may download the information from the PCB, which stores the information in the memory thereof).

The controller 110 transmits a high frequency signal to the piezoelectric motor 330, to move the piezoelectric vibrated mover 350 in an arrow direction shown in FIG. 10(*a*). When the controller 110 determines a value sensed by one of the Hall sensors 222 during movement of the piezoelectric vibrated mover 350 to be equal to one of the stored sensing values, the controller 110 stops operation of the piezoelectric motor 330 and, as such, the piezoelectric vibrated mover 350 stops. At the same time, the controller 110 controls the transducer 380 to radiate ultrasound and, as such, a thermal solidification point CA is formed in an area of the skin. In such a manner, the value sensed for each of the predetermined positions P1 to P8 is compared with the stored sensing values, and ultrasound is radiated from the transducer 380 when the sensed value is equal to one of the stored sensing values, and, as such, thermal solidification points CA may be formed at intervals of the distance d at the positions P1 to P8, respectively.

Meanwhile, after radiation of ultrasound from the transducer 380 at a final one of the predetermined positions P1 to P8, that is, the position P8, the piezoelectric vibrated mover 350 is moved for a predetermined time, to be positioned at the arrival position Pe, and, as such, formation of a series of thermal solidification points is completed. Here, the arrival position Pe may not be a position spaced apart from the position P8 by the distance d, but may be a position at which the piezoelectric vibrated mover 350 is positioned after moving for a predetermined time.

A double shot may proceed to again form thermal solidification points at the positions where a series of thermal solidification points has been formed, respectively. This process may be achieved by performing radiation of ultrasound from the position P8 to the position P1 in a reverse order while moving the piezoelectric vibrated mover 350 from the position Pe in an opposite direction.

Meanwhile, an HIFU device according to another embodiment of the present invention and a method for controlling a transducer moving piezoelectric device used in the HIFU device will be described with reference to FIG. 11.

Figure 11:
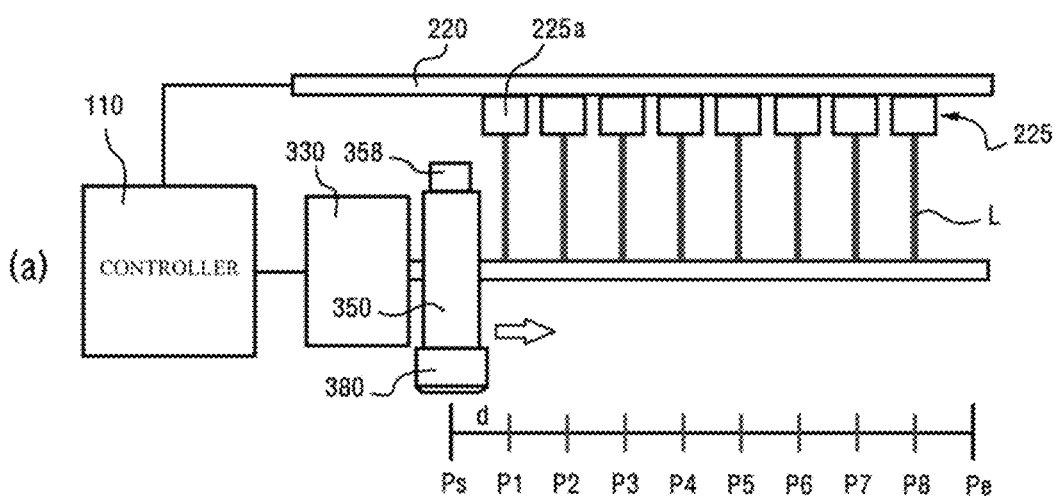
Figure 11:
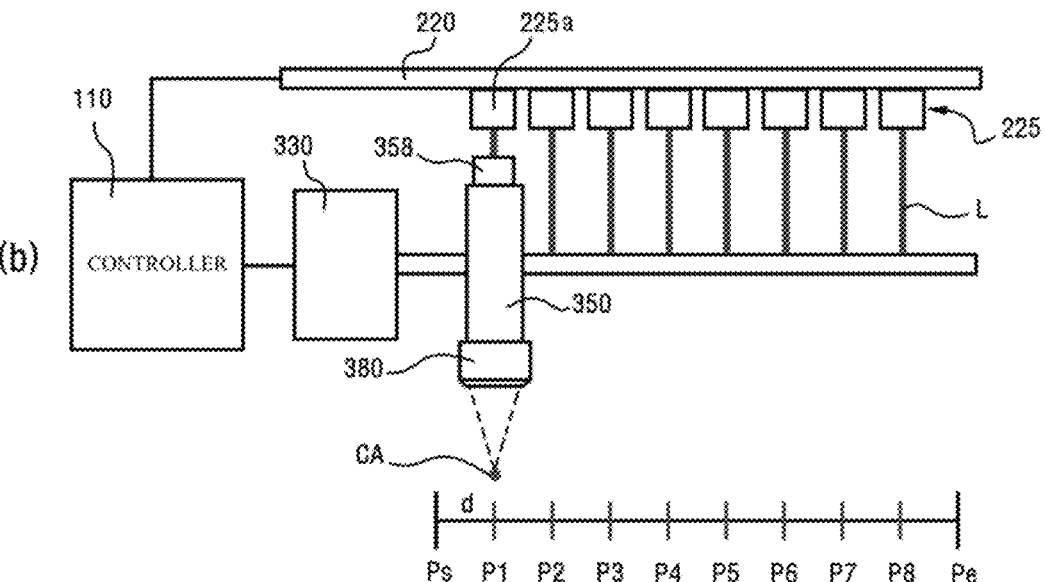

Similarly to the embodiment of FIG. 10, the embodiment illustrated in FIG. 11 provides a control method for more accurate and stable movement of the piezoelectric vibrated mover capable of eliminating the problem encountered in the embodiment illustrated in FIG. 9.

The embodiment of FIG. 11 relates to a configuration in which an optical element array unit is provided at the transducer moving piezoelectric device. In this case, the optical element array unit basically uses a first optical element, which is one of a light emitting element and a light receiving element, and a second optical element, which is the other of the light emitting element and the light receiving element. In detail, a first light element 358 is provided at one side of the piezoelectric vibrated mover 350, and an optical element array 225 including a plurality of second optical elements 225a is provided at an area facing the first optical element 358, and, as such, light reception is achieved between the first optical element 358 and one of the second optical elements 225a during movement of the piezoelectric vibrated mover 350 along the piezoelectric vibrating shaft 341.

FIG. 11(*a*) illustrates an example in which the optical element array 225 is constituted by a plurality of uniformly-spaced light emitting elements 225a arranged on the PCB 220, and a light receiving element is provided, as the optical element 358, at an end of the piezoelectric vibrated mover 350, to receive light from the light emitting elements 225a. On the contrary, the optical element array 225 may be embodied by a plurality of light receiving elements, and a light emitting element may be provided at the end of the piezoelectric vibrated mover 350.

As illustrated in FIG. 11(*a*), the light emitting elements 225a constituting the optical element array 225 may be provided at positions corresponding to the positions P1 to P8, at which the transducer 380 radiates ultrasound, respectively.

In the control method for the transducer moving piezoelectric device according to this embodiment, as illustrated in FIG. 11(*b*), the controller 110 performs a control process of:

transmitting a high frequency signal to the piezoelectric motor 330 such that the piezoelectric motor 330 generates piezoelectric ultrasound, the piezoelectric vibrating shaft 341 connected to the piezoelectric motor 330 generates vibration according to the generated piezoelectric ultrasound, and the piezoelectric vibrated mover 350 coupled to the piezoelectric vibrating shaft 341 moves along the piezoelectric vibrating shaft 341 in accordance with the vibration of the piezoelectric vibrating shaft 341; and controlling the piezoelectric vibrated mover 350 and the transducer 380 such that, every time the light receiving element 358 receives light L from one of the light emitting elements 225a during movement of the piezoelectric vibrated mover 350 along the piezoelectric vibrating shaft 341, the piezoelectric vibrated mover 350 stops at a position where the light receiving element 358 receives light (one of the positions P1 to P8), and the transducer 380 is enabled to radiate ultrasound. The movement and stop of the piezoelectric vibrated mover 350 (at the same time, ultrasound radiation through the transducer 380) are repeated from the position P1 to the position P8 (that is, the piezoelectric vibrated mover 350 stops every time the light receiving element 358 receives light from one of the light emitting elements 225a during movement of the piezoelectric vibrated mover 350, to allow radiation of ultrasound through the transducer 380). Thus, thermal solidification points CA may be formed at intervals of the distance d at the positions P1 to P8, respectively.

A double shot may proceed to again form thermal solidification points at the positions where a series of thermal solidification points has been formed, respectively. This double shot is the same as that of FIG. 10 and, as such, no description thereof will be given.

Meanwhile, an HIFU device according to another embodiment of the present invention and a method for controlling a transducer moving piezoelectric device used in the HIFU device will be described with reference to FIG. 12.

Figure 12:
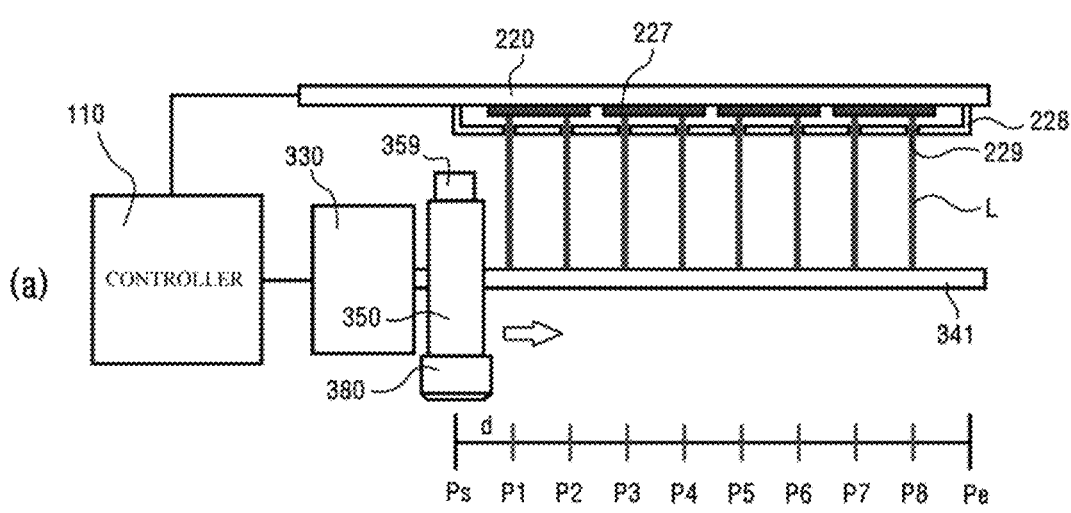
Figure 12:
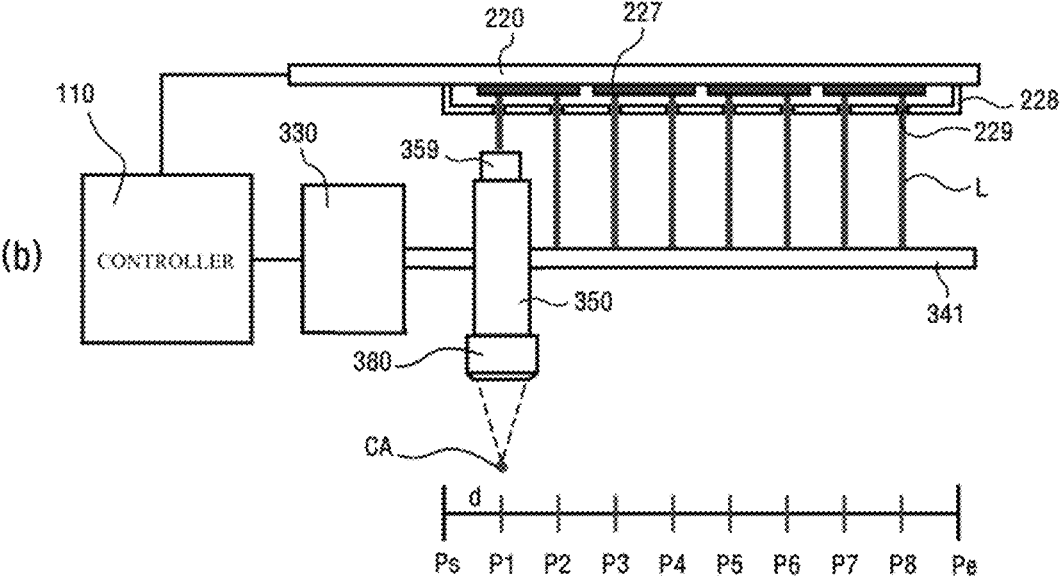

Similarly to the above-described embodiments, the embodiment illustrated in FIG. 12 provides a control method for more accurate and stable movement of the piezoelectric vibrated mover capable of eliminating the problem encountered in the embodiment illustrated in FIG. 9.

The embodiment of FIG. 12 relates to a configuration in which an optical slit unit is provided at the transducer moving piezoelectric device. In this case, the optical slit unit includes a sensor housing 228 extending along a movement path of the piezoelectric vibrated mover 350, light sources 227 disposed in the sensor housing 228, and slits 229 formed at positions of the sensor housing 228 corresponding to positions P1 to P8, at which the transducer 380 radiates ultrasound, respectively. In accordance with the configuration of the optical slit unit, light L from the light sources 229 passes through associated ones of the slits 229.

Since the piezoelectric driving unit has a very small size, there may be a difficulty in providing light emitting elements at respective positions P1 to P8 due to the size of the light emitting elements. Such a problem associated with size may be solved through a configuration in which light from one light source 227 passes through two or more slits 229.

Light L passing through the plural slits 229 formed through the sensor housing 228 in the above-described optical slit unit is received by a light receiving sensor 359 provided at an end of the piezoelectric vibrated mover 350 (FIG. 12(*a*)).

FIG. 12(*a*) illustrates a configuration in which the light sources 227 and the sensor housing 228 are provided at the PCB 220, and the slits 229 formed through the sensor housing 228 correspond to ultrasound irradiation positions, that is, positions P1 to P8, respectively.

In this embodiment, the controller 110 transmits a high frequency signal to the piezoelectric motor 330 and, as such, the piezoelectric motor 330 generates piezoelectric ultrasound, the piezoelectric vibrating shaft 341 connected to the piezoelectric motor 330 generates vibration according to the generated piezoelectric ultrasound, and the piezoelectric vibrated mover 350 coupled to the piezoelectric vibrating shaft 341 moves along the piezoelectric vibrating shaft 341 in accordance with the vibration of the piezoelectric vibrating shaft 341. During movement of the piezoelectric vibrated mover 350, the light receiving sensor 359 sequentially receives light L from the light sources 227 passing through the slits 229 of the sensor housing 228, as illustrated in FIG. 12(*b*).

When the light receiving sensor 359 receives light L, as described above, the controller 110 performs a control process for stopping the piezoelectric vibrated mover 350 at a light receiving position (one of the positions P1 to P8), and enabling the transducer 380 to radiate ultrasound. The movement and stop of the piezoelectric vibrated mover 350 (at the same time, ultrasound radiation through the transducer 380) are repeated from the position P1 to the position P8 (that is, the piezoelectric vibrated mover 350 stops every time when the light receiving element 359 receives light passing through one of the slits 229 during movement of the piezoelectric vibrated mover 350, to allow radiation of ultrasound through the transducer 380). Thus, thermal solidification points CA may be formed at intervals of the distance d at the positions P1 to P8, respectively.

A double shot may proceed to again form thermal solidification points at the positions where a series of thermal solidification points has been formed, respectively. This double shot is the same as that of FIG. 10 and, as such, no description thereof will be given.

As apparent from the above description, the present invention provides an HIFU device capable of achieving accurate and stable control as to movement of a transducer and a treatment position while achieving a great reduction in size by use of a transducer moving piezoelectric device configured to have a compact size in accordance with a great reduction in the size of a handpiece, and a method for controlling the transducer moving piezoelectric device.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A high-intensity focused ultrasound device for providing ultrasound for treatment, comprising:

a handpiece body;

a cartridge comprising a printed circuit board (PCB) with a memory storing a plurality of sensing values, the cartridge detachably coupled and electrically connected to the handpiece body, wherein the cartridge is filled with a fluid for generation of ultrasound and provided with a contact head at one side thereof to come into close contact with a skin of a subject to be treated;

a transducer that provides a high-intensity focused ultrasound for treatment in accordance with a high frequency signal;

a piezoelectric driving device provided in the fluid in the cartridge, wherein the piezoelectric driving device comprises:

a piezoelectric motor to generate piezoelectric ultrasound in accordance with the high frequency signal, a piezoelectric vibrating shaft connected to the piezoelectric motor to generate ultrasonic vibration in accordance with the piezoelectric ultrasound generated by the piezoelectric motor, a piezoelectric vibrated mover movably coupled to the piezoelectric vibrating shaft so that the transducer is coupled to the piezoelectric vibrated mover and the piezoelectric vibrated mover moves along the piezoelectric vibrating shaft in accordance with ultrasonic vibration by the piezoelectric motor to move with the transducer, a driving frame fixed to a side of a body of the cartridge, the driving frame comprising a frame body, a driving unit coupling member provided at a first side of the frame body, an operation support member provided at a second side of the frame body opposite the first side, a first guide shaft and a second guide shaft, each of which has a first end fixed to the driving unit coupling member and a second end opposite the first end fixed to the operation support member, and a body coupling hole and a plurality of engagement holes provided at the driving unit coupling member, wherein the piezoelectric motor is primarily coupled to the body coupling hole and is secondarily engaged with the plurality of engagement holes to firmly couple the piezoelectric motor with the driving unit coupling member, and a magnet provided to an end of the piezoelectric vibrated mover, wherein a plurality of magnetic field sensors is arranged on the PCB in a line along the piezoelectric vibrating shaft while being spaced apart from the magnet so as to detect a position of the transducer by detecting the magnet; and a controller configured to:

transmit a signal to the piezoelectric motor to move the piezoelectric vibrated mover along the piezoelectric vibrating shaft, control the piezoelectric motor to stop the piezoelectric vibrated mover at a stop position when a sensing value sensed by one of the plurality of magnetic field sensors generated during a movement of the piezo-electric vibrated mover reaches one of predetermined sensing values corresponding to a plurality of positions at which the transducer radiates, respectively, control the transducer to radiate the high-intensity focused ultrasound at the stop position, and control to repeat the ultrasonic vibration, the movement of the piezoelectric vibrated mover along the piezo-electric vibrating shaft, and the generation of ultrasound through the transducer so that the transducer sequentially radiates the ultrasound at the plurality of positions corresponding to the predetermined sensing values stored in the memory, wherein the PCB is disposed at an outer surface of the cartridge and electrically connects with the controller when the cartridge is coupled to the handpiece body, wherein the plurality of magnetic field sensors sense a magnetic field of the magnet, wherein a signal sensed by each of the plurality of magnetic field sensors is transmitted to the controller, and wherein the controller senses a position and the movement of the piezoelectric vibrated mover based on the signal sensed by the each of the plurality of magnetic field sensors and controls generation of the high frequency signal.

2. The high-intensity focused ultrasound device according to claim 1, further comprising a high frequency generator provided outside of the handpiece body.

3. The high-intensity focused ultrasound device according to claim 1, wherein the piezoelectric motor is coupled to the driving unit coupling member and the piezoelectric vibrating shaft, wherein a first end of the piezoelectric vibrating shaft is connected to the piezoelectric motor and a second end opposite to the first end of the piezoelectric vibrating shaft is fixed to the operation support member so that the piezoelectric vibrated mover is enabled to move with the transducer along the piezoelectric vibrating shaft between the driving unit coupling member and the operation support member in accordance with the ultrasonic vibration of the piezoelectric vibrating shaft.

4. The high-intensity focused ultrasound device according to claim 1, wherein the piezoelectric vibrated mover comprises:

an operating body;

a transducer coupling member at the operating body and coupled with the transducer; and a driving core member surrounding the piezoelectric vibrating shaft and movable along the piezoelectric vibrating shaft, wherein the piezoelectric vibrated mover further comprises:

a first slide groove formed at a first side of the operating body and the first slide groove fitted around the first guide shaft; and a second slide groove formed at a second side of the operating body and the second slide groove fitted around the second guide shaft, wherein the piezoelectric vibrated mover is guided by the first guide shaft and the second guide shaft for a stable movement of the piezoelectric vibrated mover.

* * * * *